United States Patent [19]

Markwell

[11] Patent Number: 4,460,594
[45] Date of Patent: Jul. 17, 1984

[54] BICYCLO-HETERO-ALKYLENE-1-PIPERIDINES, PHARMACEUTICAL COMPOSITIONS THEREOF AND METHODS OF USE THEREOF

[75] Inventor: Roger E. Markwell, Great Dunmow, England

[73] Assignee: Beecham Group p.l.c., England

[21] Appl. No.: 418,267

[22] Filed: Sep. 15, 1982

[30] Foreign Application Priority Data

Sep. 17, 1981 [GB] United Kingdom ................. 8128090
Sep. 17, 1981 [GB] United Kingdom ................. 8128091

[51] Int. Cl.³ ................... A61K 31/445; C07D 417/06
[52] U.S. Cl. .................................... 424/267; 424/258;
546/139; 546/153; 546/155; 546/157; 546/170;
546/174; 546/176; 546/177; 546/179; 546/196;
546/201; 546/202; 546/147; 546/156; 546/178
[58] Field of Search ............... 546/147, 139, 174, 176,
546/201, 202, 196, 153, 155, 156, 157, 170, 177,
178, 179; 424/258, 267

[56] References Cited

U.S. PATENT DOCUMENTS 3,558,637  1/1971  Kaiser et al. ........................ 546/202
3,936,464  2/1976  Allen et al. ......................... 546/201
4,358,456  11/1982 Ward ................................. 546/201

Primary Examiner—Robert T. Bond

Attorney, Agent, or Firm—Jacobs & Jacobs

[57] ABSTRACT

Compounds of the formula (I), and pharmaceutically acceptable salts thereof:

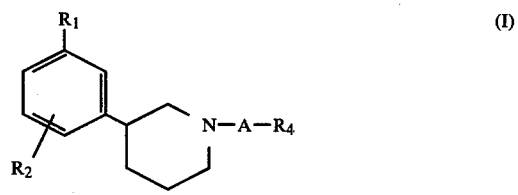

(I)

wherein:
$R_1$ is hydroxy, $C_{1-4}$ alkoxy or an in-vivo hydrolysable acyloxy group:
$R_2$ is hydrogen, $C_{1-4}$ alkyl, hydroxy, $C_{1-4}$ alkoxy or an in-vivo hydrolysable acyloxy group;
$R_4$ is benzofuryl, benzothienyl, indolyl, quinolyl, isoquinolyl, 2,3-dihydrobenzofuryl, 2,3-dihydrobenzylthienyl or 2,3-dihydroindolyl optionally substituted by one or two substituents selected from $C_{1-4}$ alkoxy, hydroxy or acyloxy, trifluoromethyl, halogen or nitro; and
A is a bond or $C_{1-6}$ alkylene,
a process for their preparation, and pharmaceutical compositions containing them.

21 Claims, No Drawings

BICYCLO-HETERO-ALKYLENE-1-PIPERIDINES, PHARMACEUTICAL COMPOSITIONS THEREOF AND METHODS OF USE THEREOF

This invention relates to novel compounds to pharmaceutical compositions containing them, and to a process for their preparation.

Racemic 3-(3-hydroxyphenyl)-N-n-propylpiperidine (3-PPP) is a known dopamine agonist which at lower dosages acts predominantly at presynaptic dopamine autoreceptors. At higher dosages one enantiomer acts as a postsynaptic dopamine agonist, whilst the other acts as a postsynaptic dopamine antagonist. This compound is thus of potential use in the treatment of CNS disorders related to excess dopamine release.

We have now discovered a class of structurally distinct compounds which are similarly useful in the treatment of such disorders.

The present invention provides a compound of the formula (I), and pharmaceutically acceptable salts thereof:

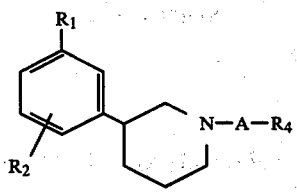

(I)

wherein:
$R_1$ is hydroxy, $C_{1-4}$ alkoxy or an in-vivo hydrolysable acyloxy group:
$R_2$ is hydrogen, $C_{1-4}$ alkyl, hydroxy, $C_{1-4}$ alkoxy or an in-vivo hydrolysable acyloxy group;
$R_4$ is benzofuryl, benzothienyl, indolyl, quinolyl, isoquinolyl 2,3-dihydrobenzofuryl, 2,3-dihydrobenzylthienyl or 2,3-dihydroindolyl optionally substituted by one or two substituents selected from $C_{1-4}$ alkoxy, hydroxy or acyloxy, trifluoromethyl, halogen or nitro; and
A is a bond or $C_{1-6}$ alkylene.

Examples of $R_1$ and $R_2$ include hydroxyl, methoxy, ethoxy, n- and iso-propoxy and in-vivo hydrolysable acyloxy groups, such as $C_{1-6}$ alkanoyloxy, for example acetoxy, propionoxy, and n- and iso-butyroxy,2,2-dimethylpropanoyloxy, benzoyloxy optionally substituted in the phenyl ring by one or two substituents selected from $C_{1-4}$ alkyl, $C_{1-4}$ alkoxy, trifluoromethyl, halogen or nitro, and labile sulphonate groups for example $C_{1-4}$ alkanesulphonyloxy, e.g. methanesulphonyloxy, or benzenesulphonyloxy optionally substituted as for benzoyloxy above, e.g. toluenesulphonyloxy.

$R_2$ may also be hydrogen or $C_{1-4}$ alkyl. Suitable $C_{1-4}$ alkyl groups include methyl, ethyl and n- and iso-propyl, preferably methyl.

$R_1$ and/or $R_2$ will often be hydroxyl, methoxy, 2-2-dimethylpropanoyloxy or benzoyloxy.

$R_2$ will often be hydrogen or the same as $R_1$. $R_2$ will usually be in the 4- or 5-poisitions (standard numbering for the phenyl ring system).

$R_4$ may be benzofuryl, benzothienyl, indolyl, quinolyl, isoquinolyl, 2,3-dihydrobenzofuryl, 2,3-dihydrobenzothienyl or 2,3-dihydroindolyl optionally substituted as hereinbefore defined.

The $R_4$ bond to the rest of the molecule may be at any substitutable atom of the $R_4$ group, that is at any except the bridgehead and hereto-atoms (except for indolyl or 2,3-dihydroindolyl nitrogen).

Suitable optional substituents in the heterocycle include $C_{1-4}$ alkyl, such as methyl ethyl and n- and isopropyl, preferably methyl; and halogen such as chloro and bromo.

Suitable and preferred optional substituents in the benzo moiety include those in the preceding paragraph and $C_{1-4}$ alkoxy, such as methoxy, ethoxy and n- and isopropoxy, preferably methoxy; hydroxy; in-vivo hydrolysable acyloxy as described for $R_1$ and $R_2$; trifluoromethyl; and nitro.

When two substituents are in the same ring they are usually the same.

When the $R_4$ bond to the rest of the molecule is at a benzo atom, it is preferred that the heterocycle is substituted.

$R_4$ will often be unsubstituted, and bonded via the heterocycle, often to the 2- or 3- position (based on standard optionally hydrogenated heteroarene numbering).

A may suitably be a bond or $C_{1-4}$ polymethylene optionally substituted by one or two methyl groups. A will often be methylene or ethan-1,2-diyl.

The compounds of the formula (I) may form acid addition salts at the $R_4$ nitrogen atom when $R_4$ is 2,3-dihydroindolyl or at the

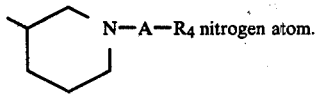

The pharmaceutically acceptable salts of the compounds of the formula (I) include acid addition salts with conventional acids such as hydrochloric, hydrobromic, phosphoric, sulphuric, citric, tartaric, lactic and acetic acid and the like.

The compounds of the formula (I) and their pharmaceutically acceptable salts can also form solvates and the invention extends to such solvates.

All compounds of formula (I) have a chiral centre at the piperidine 3-position. Additionally, partially saturated 2- or 3-$R_4$ derivatives are chiral at those positions, and A may contain a chiral centre, as may $R_1$ and $R_2$ and $R_4$ substituents. This invention extends to all isomers including enantiomers of the compounds of formula (I) and to mixtures thereof including racemates.

A group of compounds within those of formula (I) is of formula (II):

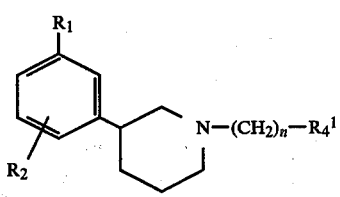

(II)

wherein: $R_4^1$ is benzofuryl, benzothienyl, indolyl, quinolyl or isoquinolyl, optionally substituted as defined: n is 0 to 4; and the remaining variables are as defined in formula (I).

Suitable and preferred $R_1$ and $R_2$ are as so described under formula (I). n is often 1 or 2.

Suitable and preferred $R_4^1$ are as so described under formula (I) for corresponding $R_4$.

A group of compounds within those of formula (II) is of formula (III):

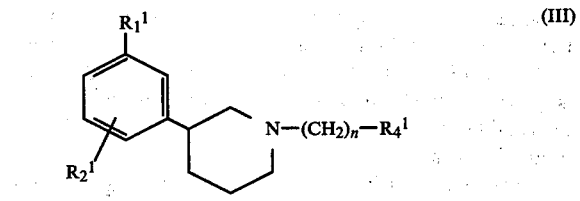

(III)

wherein:
$R_1^1$ is hydroxyl or an in-vivo hydrolysable acyloxy group;
$R_2^1$ is hydrogen, $C_{1-4}$ alkyl, hydroxyl or an in-vivo hydrolysable acyloxy group;
and the remaining variables are as defined in formula (II).

Suitable and preferred $R_1^1$ and $R_2^1$ are hydrogen, hydroxyl and as so described under formula (I) for $R_1$ and $R_2$ in-vivo hydrolysable acyloxy.

Suitable and preferred n and $R_4^1$ are as so described under formula (II).

A second group of compounds within those of formula (II) is of formula (IV):

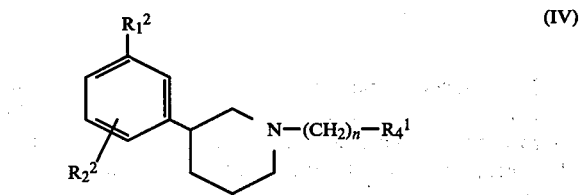

(IV)

wherein:
$R_1^2$ is $C_{1-4}$ alkoxy;
$R_2^2$ is hydrogen, $C_{1-4}$ alkyl or $C_{1-4}$ alkoxy; and
the remaining variables are as defined in formula (II).

Suitable and preferred $R_1^2$ and $R_2^2$ are hydrogen, and as so described for $R_1$ and $R_2$ $C_{1-4}$ alkoxy under formula (I).

Suitable and preferred n and $R_4^1$ are as so described under formula (III).

A third group of compounds within those of formula (II) is of formula (V):

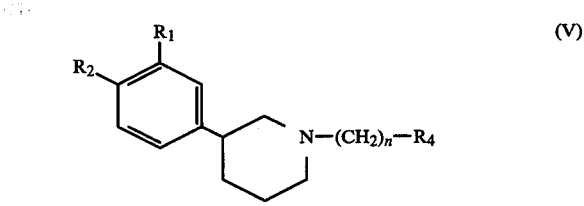

(V)

wherein: the variables are as defined in formula (II).

Suitable and preferred $R_1$, $R_2$, $R_4^1$ and n are so described under formula (II).

A sub-group of compounds within those of formula (V) is of formula (VI):

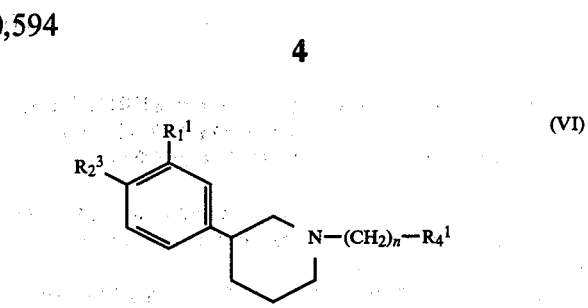

(VI)

wherein: $R_2^3$ independently of $R_1^1$ is $C_{1-4}$ alkoxy; and other variables are as defined in formula (III).

Suitable and preferred variables are as so described under formula (III).

A second sub-group of compounds within those of formula (V) is of formula (VII):

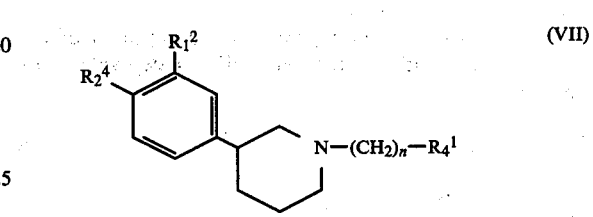

(VII)

wherein:
$R_2^4$ independently of $R_1^2$ is hydroxy or in-vivo hydrolysable acyloxy;
and other variables are as defined in formula (IV).

Suitable and preferred variables are as so described under formula (IV).

A third sub-group of compounds within those of formula (V) is of formula (VIII):

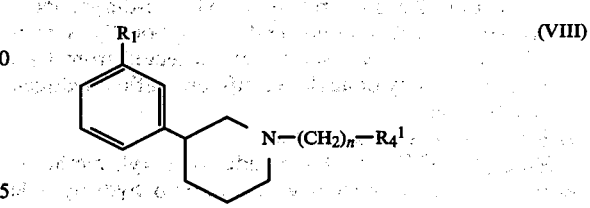

(VIII)

wherein: the variables are as defined in formula (II).

Suitable and preferred variables are as so described under formula (II).

A sub-group of compounds within those of formula (VIII) is of formula (IX):

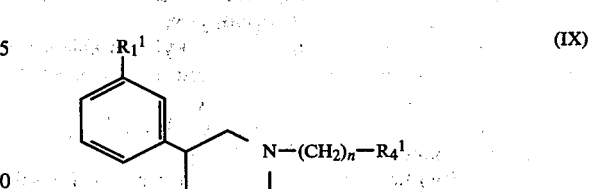

(IX)

wherein: the variables are as defined in formula (III).

Suitable and preferred variables are as so described under formula (III).

A second sub-group of compounds within those of formula (VIII) is of formula (X):

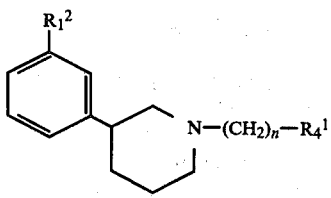

wherein: the variables are as defined in formula (IV).

Suitable and preferred variables are as so described under formula (IV).

A third sub-group of compounds within those of formula (VIII) is of formula (XI)

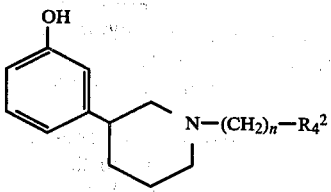

wherein, $R_4^2$ is benzofuryl or indolyl, optionally substituted on the heterocycle by $C_{1-4}$ alkyl or halogen, and n is 0 to 4.

Suitable and preferred $R_4^2$ are as so described for corresponding $R_4$ under formula (I).

A fourth group of compounds within those of formula (I) is of formula (XII):

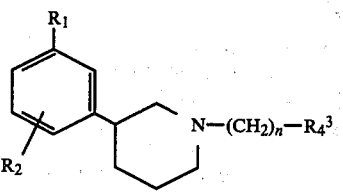

wherein, $R_4^3$ is 2,3-dihydrobenzofuryl, 2,3-dihydrobenzothienyl or 2,3-dihydroindolyl optionally substituted as defined; n is 0 to 4; and the remaining variables are as defined in formula (I).

Suitable and preferred $R_1$, $R_2$ and $R_4^3$ are as so described for $R_1$, $R_2$ and corresponding $R_4$ under formula (I). n is often 1 or 2.

A group of compounds within those of formula (XII) is of formula (XIII);

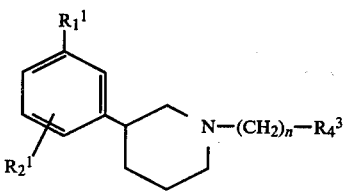

wherein, $R_1^1$ is hydroxyl or an in-vivo hydrolysable acyloxy group;

$R_2^1$ is hydrogen, $C_{1-4}$ alkyl, hydroxyl or an in-vivo hydrolysable acyloxy group;

and the remaining variables are as defined in formula (XII).

Suitable and preferred $R_1^1$ and $R_2^1$ are hydrogen, hydroxyl and as so described under formula (I) for $R_1$ and $R_2$ in-vivo hydrolysable acyloxy.

Suitable and preferred n and $R_4^3$ are as so described under formula (XII).

A second group of compounds within those of formula (XII) is of formula (XIV);

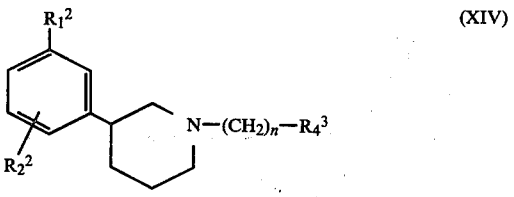

wherein, $R_1^2$ is $C_{1-4}$ alkoxy;

$R_2^2$ is hydrogen $C_{1-4}$ alkoxy; and the remaining variables are as defined in formula (XII).

Suitable and preferred $R_1^2$ and $R_2^2$ are hydrogen, and as so described for $R_1$ and $R_2$ $C_{1-4}$ alkoxy under formula (I).

Suitable and preferred n and $R_4^3$ are as so described under formula (XII).

A third group of compounds within those of formula (XII) is of formula (XV):

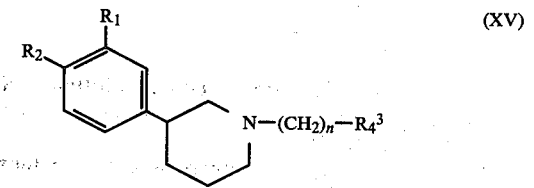

wherein: the variables are as defined in formula (XII).

Suitable and preferred $R_1$, $R_2$, $R_4^3$ and n are so described under formula (XII).

A sub-group of compounds within those of formula (XV) is of formula (XVI):

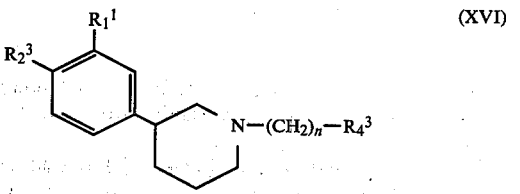

wherein: $R_2^3$ independently of $R_1^1$ is $C_{1-4}$ alkoxy; and other variables are as defined in formula (XIII).

Suitable and preferred variables are as so described under formula (XIII).

A second sub-group of compounds within those of formula (XV) is of formula (XVII):

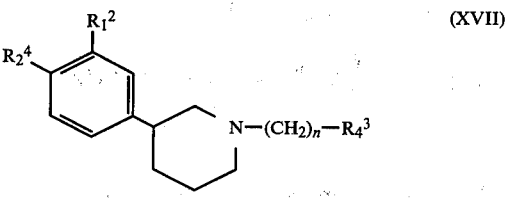

wherein:

$R_2^4$ independently of $R_1^2$ is hydroxy or in-vivo hydrolysable acyloxy; and other variables are as defined in formula (XIV).

Suitable and preferred variables are as so described under formula (XIV).

A third sub-group of compounds within those of formula (XV) is of formula (XVIII):

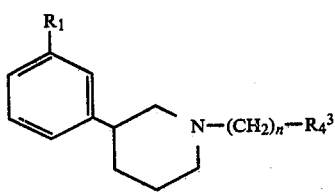

(XVIII)

wherein: the variables are as defined in formula (XII).

Suitable and preferred variables are as so described under formula (XII).

A sub-group of compounds within those of formula (XVIII) is of formula (XIX):

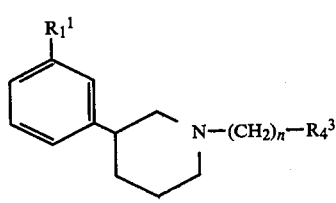

(XIX)

wherein: the variables are as defined in formula (XIII).

Suitable and preferred variables are as so described under formula (XIII).

A second sub-group of compounds within those of formula (XVIII) is of formula (XX):

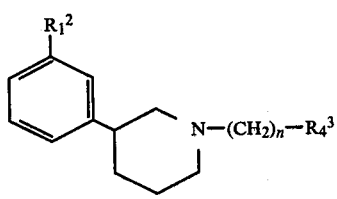

(XX)

wherein: the variables are as defined in formula (XIV).

Suitable and preferred variables are as so described under formula (XIV).

The compound of the formula (I) is conveniently prepared by the reaction of a compound of the formula (XXI):

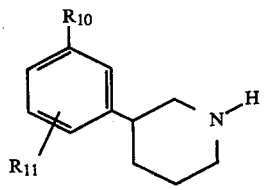

(XXI)

with a compound of the formula (XXII):

(XXII)

wherein:

$R_{10}$ is hydroxy or protected hydroxyl;

$R_{11}$ is hydrogen, $C_{1-4}$ alkyl, hydroxy or protected hydroxy;

L is a bond, $C_{1-6}$ alkylene, or $C_{1-6}$ 1-oxoalkylene where Q is at and defines the 1-position;

Q is a group readily displaceable by a nucleophile; and $R_4$ is as defined in formula (I):

and as necessary reducing L $C_{1-6}$ 1-oxoalkylene to A; as desired or necessary converting $R_{10}$ or $R_{11}$ to $R_1$ or $R_2$ respectively; converting $R_1$ $R_2$ or $R_4$ to other $R_1$ $R_2$ or $R_4$; and optionally salifying the resulting compound of the formula (I).

This process forms an aspect of the present invention.

It will be appreciated by the skilled man that an $R_{10}$ or $R_{11}$ protected hydroxyl group is a conventional group readily convertible after a desired reaction to a hydroxyl group.

Examples of $R_{10}$ or $R_{11}$ when protected hydroxyl include $C_{1-4}$ alkoxy and in-vivo hydrolysable acyloxy as defined and described for $R_1$ and $R_2$ in and under formula (I); and benzyloxy optionally substituted in the phenyl ring as for $R_4$.

L when a bond or $C_{1-6}$ alkylene corresponds to A as hereinbefore defined. When $C_{1-6}$ 1-oxoalkylene as defined, L forms an N-($R_4$-alkanoyl) derivative of the compound of the formula (XII) which may be reduced to the corresponding compound of the formula (I). It will be appreciated that this process variant is only applicable to compounds of the formula (I) having an A group with an unsubstituted methylene bound to the piperidine nitrogen atom.

Suitable examples of Q include halide such as Cl, Br or I. When L is a bond or $C_{1-6}$ alkylene Q may also be labile sulphonate such as $-OSO_2CH_3$ or $-O-SO_2.C_6H_4.p-CH_3$. When L is $C_{1-6}$ 1-oxoalkylene Q may also be $C_{1-6}$ alkanoyloxy such as acetoxy.

The condensation of the compounds of the formulae (XXI) and (XXII) is conveniently effected in an inert aprotic solvent such as an ether, for example THF, or a halohydrocarbon, for example dichloromethane, or in a mixture of such solvents, at a non-extreme temperature such as ambient to solvent boiling point. Other solvents include DMF, DMSO and acetonitrile.

The reaction generally eliminates an acid, and it is thus often preferable to effect it in the presence of a base such as a mild inorganic base, for example potassium carbonate or a stronger organic base, for example triethylamine.

When $R_{10}$ or $R_{11}$ when a protected hydroxyl group, is of the form $R_{12}O$, where $R_{12}$ is $C_{1-4}$ alkyl, conversion of $R_{10}$ or $R_{11}$ to $R_1$ or $R_2$ hydroxyl respectively is conveniently effected by conventional methods, such as by warming with aqueous hydrobromic acid. Alternatively this may be carried out by treatment with pyridine hydrochloride, boron tribromide or boron triiodide or iodotrimethylsilane.

When $R_{12}$ is $C_{1-6}$ alkanoyl or benzoyl optionally substituted as defined deprotection may be effected conventionally, for example by acidic or basic hydrolysis.

When $R_{12}$ is optionally substituted benzyl as defined above conversion is conveniently effected by conventional methods such as transition metal catalysed hydrogenolysis using for example palladium—or platinum—charcoal, at atmospheric pressure or a slight excess thereover.

Compounds of the formula (I) wherein $R_1$ and optionally $R_2$ are $C_{1-4}$ alkoxy or in-vivo hydrolysable acyloxy are derivable from those wherein $R_1$ and $R_2$ are hydroxy by conventional O-alkylation or esterification reactions respectively.

The reaction may be carried out under conventional O-alkylation conditions, using a compound of the formula $R_{12}{}^1Q$ where $R_{12}{}^1$ is $C_{1-4}$ alkyl and Q is a group readily displaced by a nucleophile. Suitable examples of Q include halide such as Cl, Br or I or labile sulphonate groups such as $OSO_2CH_3$ or $OSO_2.C_6H_4.p\ CH_3$.

The reaction is generally effected in an inert solvent, at a non-extreme temperature such as ambient or slightly elevated temperature, for example solvent reflux temperature.

It will be appreciated by the skilled man that O-alkylation or O-acylation of compounds of the formula (I) may also lead to quaternary N-alkylation of the piperidine nitrogen atom or tertiary or quaternary N-alkylation of an $R_4$ nitrogen atom when present unless these nitrogen atoms are protected, for example by carrying out acylation in the presence of a strong acid such as trifluoroacetic acid, so that the —NH— function is protected by protonation. The acid may conveniently also act as the solvent. Alternatively the $R_4$ nitrogen atom may be protected by a conventional N- protecting group, as discussed hereinafter.

For in-vivo hydrolysable esters the reaction may be carried out under conventional esterification conditions using a compound of the formula $R_{12}{}^2W$ wherein $R_{12}{}^2$ is an acyl group capable of forming an in-vivo hydrolysable acyloxy group and W is for example halide, such as chloride; acyloxy, such as $C_{1-4}$ alkanoyloxy; or hydroxyl.

$R_{12}{}^2$ may typically be the acyl group corresponding to $R_1$ and $R_2$ in-vivo hydrolysable acyloxy groups described under formula (I).

When W is halide the reaction is generally carried out in the presence of a base; when W is hydroxyl it is generally effected in the presence of a dehydrating agent such as dicyclohexylcarbodiimide.

The reaction is generally effected in an inert solvent at non-extreme temperatures such as ambient or slightly elevated temperature, for example solvent reflux temperature.

$R_4$ benzofuryl or optionally N-protected indolyl may be converted to 2,3-dihydrobenzofuryl or 2,3-dihydroindolyl by reduction.

Reduction is conveniently effected by transition-metal catalysed hydrogenation for example using palladium or platinum/charcoal or platinum (IV) oxide, or Raney nickel, at atmospheric pressure of hydrogen or a slight excess thereover. Hydrogenolyable $R_{10}{}^1$, $R_{11}{}^1$ or N-protecting group in $R_4$ may also be simultaneously removed. Alternatively, for $R_4$ indolyl, a moderate complex hydride may be used, for example sodium borohydride in trifluoroacetic acid or borane-amine complexes such borane-trimethylamine or borane-pyridine. Diborane in trifluoroacetic acid may also be used.

It will be appreciated that all the above interconversions may also be carried out in the products of the reaction of the compounds of formulae (XXI) and (XXII) which are not of formula (I) or in the compounds of formulae (XXI) and (XXII) themselves.

From the foregoing it will be appreciated that this invention also provides a second process for the preparation of a compound of the formula (I) or a pharmaceutically acceptable salt thereof, which process comprises the deprotection of a compound of the formula (XXIII):

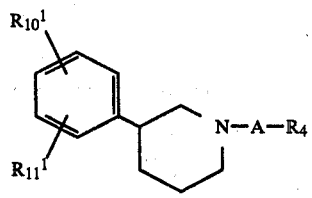

wherein:
$R_{10}{}^1$ is protected hydroxy;
$R_{11}{}^1$ is hydrogen, $C_{1-4}$ alkyl or protected hydroxyl; and the remaining variables are as defined in formula (I); and thereafter optionally O-alkylating or O-acylating with an acyl group capable of forming an in-vivo hydrolysable acyloxy group the resultant compound of the formula (I); and optionally salifying the resultant compound of the formula (I).

Suitable process conditions are as so described for the relevant first-process steps hereinbefore.

From the foregoing it will be appreciated that this invention also provides a process for the preparation of a compound within formula (I) of the formula (XXIV) or a pharmaceutically acceptable salt thereof:

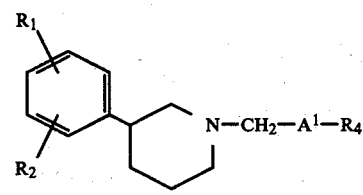

wherein: $A^1$ is a bond or $C_{1-5}$ alkylene and the remaining variables are as defined in formula (I), which process comprises the reduction of a compound of the formula (XXV)

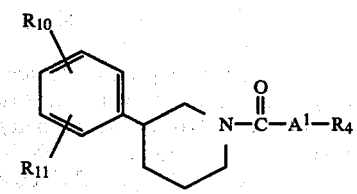

and thereafter as desired or necessary converting $R_{10}$ or $R_{11}$ to $R_1$ or $R_2$ respectively; optionally converting $R_1$, $R_2$ or $R_4$ to other $R_1$, $R_2$ or $R_4$; and optionally salifying the resulting compound of the formula (I).

The reduction of the compound of the formula (XXV) is conveniently effected with a strong reducing agent, such as a strong inorganic complex hydride, for example lithium aluminium hydride.

If a strong inorganic complex hydride reductant is used, the reaction is generally carried out in a dry, aprotic polar solvent, such as dry THF or diethyl ether. Non-extreme temperatures at about ambient are suitable.

Optional steps are discussed hereinbefore and hereinafter.

A process for the preparation of a compound of the formula (I) wherein $R_4$ is 2,3-dihydrobenzofuryl or 2,3-dihydroindolyl, or a pharmaceutically acceptable salt thereof, comprises the reduction of a compound of the f formula (XXVI):

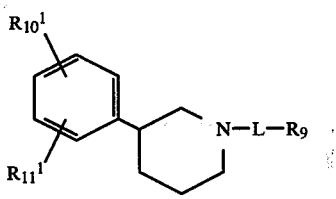

(XXVI)

wherein: $R_9$ is benzofuryl or optionally N-protected indolyl, optionally substituted as for $R_4$ and other variables are as hereinbefore defined; and thereafter as necessary reducing L $C_{1-6}$ 1-oxoalkylene to A; as desired or necessary convering $R_{10}$ or $R_{11}$ to $R_1$ or $R_2$ respectively, and $R_1$ or $R_2$ to other $R_1$ or $R_2$; and optionally salifying the resulting compound of the formula (I).

Reduction is conveniently effected as hereinbefore described.

The invention provides a process for the preparation of a compound of the formula (I) wherein $R_4$ contains an —NH—group, which process comprises the N-deprotection of a compound of the formula (XXVII):

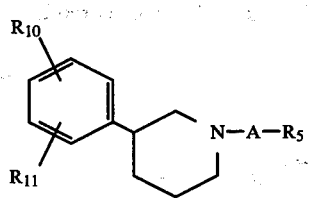

(XXVII)

wherein:
$R_5$ is N-protected indolyl or optionally substituted dihydroindolyl as defined; and the remaining variables are as defined in formula (XXII).

$R_4$ indolyl or dihydroindolyl when N-protected will contain a moiety of the form —$NR_{13}$— where $R_{13}$ is an N-protecting group. $R_{13}$ is of course a conventional group readily convertible after a desired reaction to a hydrogen atom.

Examples of $R_{13}$ N-protecting groups include $C_{1-6}$ alkanoyl, for example acetyl, propionyl n- and iso-butyryl and 2,2-dimethylpropanoyl, benzoyl optionally substituted in the phenyl ring by one or two substituents selected from $C_{1-4}$ alkyl, $C_{1-4}$ alkoxy, trifluoromethyl, halogen or nitro; $C_{1-4}$ alkoxycarbonyl, for example tert-butoxycarbonyl; benzyl optionally substituted as for benzoyl above.

When $R_{13}$ is $C_{1-6}$ alkanoyl or optionally substituted benzoyl as defined conversion to hydrogen is conveniently effected by conventional base hydrolysis. $R_{13}$ $C_{1-4}$ alkoxycarbonyl is removable by acidolysis.

When $R_{13}$ is optionally substituted benzyl as defined, conversion to hydrogen may be carried out conventionally, for example by hydrogenolysis. Suitable reaction conditions are as so described for $R_{10}/R_{11}$ hydrogenolysis.

When $R_{13}$ is formally $H_2+X^-$ as defined deprotection is conveniently effected by basification to neutral.

It will be appreciated by the skilled man that when $R_{10}$ or $R_{11}$ is protected hydroxyl conversion of $R_{13}$ to hydrogen may also convert $R_{10}$ or $R_{11}$ to hydroxyl. $R_{10}$, $R_{11}$ and $R_{13}$ and N-deprotection reaction conditions will be chosen to avoid this, if desired.

Compounds of the formula (XXI) are known e.g. from M. Julia et al., Bull. Soc. Chim. Fr. 1968, 1000, or derivable from known compounds by O-protection under conditions as described hereinbefore.

It will be appreciated that the need for N-protection is such O-protection reactions also extends to 0-acylation.

Compounds of the formula (XXII) are known compounds or may be conventionally prepared by analogy with known compounds.

By way of example, we have found that a modification of the literature methods given in R. Adams and R. E. Rindfusz, J. Amer. Chem. Soc, 41. 648 (1919) and H. Normant, Ann Chim 17, 335 (1942) is suitable for the preparation of the compounds of formula (XVI) having 2-side chain substitution. For the sake of simplicity this synthesis is shown below schematically:

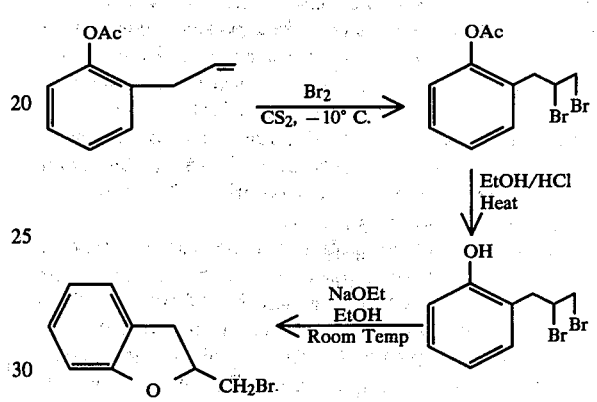

The compounds of the formula (I) may be synthesised from racemates of the compounds of formulae (XXII) or (XXIII) as appropriate, and diastereomers separated conventionally, e.g. by chromatography or fractional crystallisation, or enantiomers resolved conventionally e.g. by salification with a chiral acid and salt separation. Alternatively specific isomers or enantiomers may be obtained by using chiral starting materials.

The compounds of the formula (I) are α-adrenoceptor and dopamine agonists. Some are also α-adrenoceptor agonists.

The compounds may act at both presynaptic and postsynaptic receptors. Depending on their balance between action at presynaptic dopamine autoreceptors and action at postsynaptic dopamine receptors respectively, the compounds may be used in the treatment of central nervous system disorders related to excess dopamine release, such as psychosis, for example schizophrenia, and Huntington's chorea, and hyperkinetic and dyskinetic disorders, or in the treatment dopamine release, such as Parkinson's disease and hyperprolactinaemic syndromes.

As dopamine agonists, the compounds may also be used as mood modifiers in the treatment of CNS disorders, in particular the treatment of anxiety.

In common with other agonists, including the (—) enantiomer of the presynaptically acting dopamine agonist 3-PPP, compounds of the formula (I) may be dopamine antagonists, in particular acting post-synaptically, at higher doses, that is at doses towards the upper end of the dosage ranges mentioned hereinafter. As postsynaptic dopamine antagonists the compounds may be used in the treatment of dopamine-excess related disorders, such as described above.

The particular profile of any given compound may be readily ascertained by routine pharmacological tests of the types described hereinafter or well-known to the skilled man. Thus for example agonist activity at presynaptic autoreceptors may be ascertained by the compound's inhibition of spontaneous climbing behaviour in the mouse; agonist activity at postsynaptic receptors by an increase in spontaneous climbing behaviour in the mouse; and antagonist activity at postsynaptic receptors by inhibition of apomorphine (dopamine agonist) induced climbing behaviour in the mouse.

Compounds of the formulae (V) and (XV) wherein $R_2$ is $R_1$ as defined are believed to have an activity profile in which postsynaptic agonist activity is substantial.

Compounds of the formulae (VIII) and (XVIII) are believed to have an activity profile in which presynaptic activity predominates, in some cases to the extent that they may be regarded as selectively presynaptic.

The invention therefore also provides a pharmaceutical composition comprising a compound of the formula (I), a pharmaceutically acceptable salt thereof, or a solvate of the compound or its salt, together with a pharmaceutically acceptable carrier. Such compositions may be adapted for oral or parenteral administration, and as such may be in the form of tablets, capsules, oral liquid preparations, powders, granules, lozenges, reconstitutable powders, injectable and infusable solutions or suspensions; the compositions may also be in the form of suppositories. Normally, orally administrable compositions are preferred.

Tablets and capsules for oral administration may be in unit dose presentation form, and may contain conventional excipients such as binding agents, fillers, tabletting lubricants, disintegrants and acceptable wetting agents and the like. The tablets may be coated according to methods well known in normal pharmaceutical practice. Oral liquid preparations may be in the form of, for example, aqueous or oily suspensions, solutions, emulsions, syrups, or elixirs, or may be presented in a dry product of reconstitution with water or other suitable vehicle before use. Such liquid preparations may contain conventional additives such as suspending agents, emulsifying agents, non-aqueous vehicles (which may include edible oils), preservatives, and if desired conventional flavouring or colouring agents.

For parenteral administration, fluid unit dosage forms are prepared utilizing the compound of the formula (I) and a sterile vehicle. The compound, depending on the vehicle and concentration used, can be either suspended or dissolved in the vehicle. In preparation solutions the compound can be dissolved for injection and filter sterilized before filling into a suitable vial or ampoule and sealing. Advantageously, adjuvants such as a local anaesthetic, preservatives and buffering agents can be dissolved in the vehicle. Parenteral suspensions are prepared in substantially the same manner except that the compound is suspended in the vehicle instead of being dissolved and sterilized by exposure to ethylene oxide before suspending in the sterile vehicle. Advantageously, a surfactant or wetting agent is included in the composition to facilitate uniform distribution of the compound.

As is common practice, the compositions will usually be accompanied by written or printed directions for use in the medical treatment concerned.

It will of course be realised that the precise dosage used in the treatment of any of the hereinbefore described disorders will depend on the actual compound of the formula (I) used, and also on other factors such as the seriousness of the disorder being treated.

The invention further provides a method of treatment of dopamine-dependent CNS disorders in mammals including humans comprising the administration of an effective amount of a compound of the formula (I) or a pharmaceutically acceptable salt thereof, or a solvate of the compound or its salt. The "effective amount" will depend in the usual way on a number of factors such as the nature and severity of the malady to be treated, the weight of the sufferer, and the actual compound used.

However by way of illustration, unit does will suitably contain 0.01 to 20 mg of the compound of formula (I), for example 0.02 to 10 mg.

Again by way of illustration, such unit doses will suitably be administered more than once a day, for example 2, 3, 4, 5 or 6 times a day, in such a way that the total daily dose is suitably in the range 0.005 to 10 mg/kg per day.

The following Examples illustrate the preparation of compounds of formula (I), and the following Descriptions illustrate the preparation of intermediates therefor.

EXAMPLE 1

1-(2-Bromo-3-benzofurylmethyl)-3-(3-methoxyphenyl)-piperidine hydrochloride (1) and
1-(3-benzofurylmethyl)-3-(3-methoxyphenyl)piperidine hydrochloride (2)

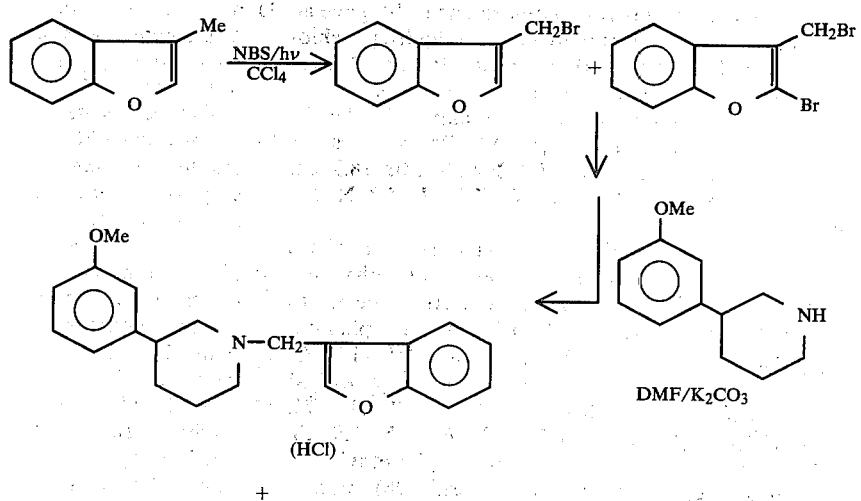

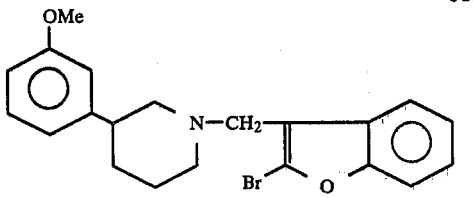

A solution of 3-methylbenzofuran (4.0 g) and N-bromosuccinimide (NBS) (7.4 g) in carbon tetrachloride (50 ml) was heated under reflux under nitrogen for 10 hour with illumination from an 100W tungsten light source. The solution was cooled, filtered and evaporated to dryness. The residue was a mixture of 3-bromomethylbenzofuran and 2-bromo-3-bromomethyl-benzofuran (4.5 g) [δ (CCl₄) 4.4 (s)]. The mixture (2.5 g) was added dropwise to a well stirred solution of (3-methoxyphenyl)-3-piperidine (2.0 g) in DMF (25 ml) and anhydrous potassium carbonate (5 g) at room temperature. After 0.5 hours the mixture was evaporated to dryness in vacuo and the residue was partitioned between dichloromethane and water. The dichloromethane layer was washed with water, dried (Na₂SO₄) and chromatographed on alumina (Grade II, 200 g). Elution of the column with ethyl acetate-pentane (1:19) gave an oil which after treatment with ethanolic-hydrogen chloride crystallised from ethyl acetate to afford 1-(2-Bromo-3-benzofurylmethyl)-3-(3-methoxyphenyl)-piperidine hydrochloride (1) (0.7 g), m.p. 157°–159° C. (Found: M+ 399.0812. $C_{21}H_{22}NO_2Br$ requires M 399.0832). (Found: C, 57.85; H, 5.2; N, 3.1; Br, 18.3; Cl, 7.95. $C_{21}H_{22}NO_2Br \cdot HCl$ needs: C, 57.75; H, 5.3; N, 3.2; Br, 18.3; Cl, 8.1%).

Further elution with ethyl acetate-pentane (1:19) gave an oil, which after treatment with ethanolic-hydrogen chloride, crystallised from ethyl acetate to afford 1-(3-benzofurylmethyl)-3-(3-methoxyphenyl)-piperidine hydrochloride (2) (1.3 g), m.p. 169°–171° C. (Found: M³⁰ 321.1743. $C_{21}H_{23}NO_2$ requires M 321.1729). (Found: C, 70.45; H, 6.8; N, 3.9; Cl, 9.75. $C_{21}H_{23}NO_2 \cdot HCl$ requires C, 70.5; H, 6.75; N, 3.9; Cl, 9.9%). 1-(2,3-Dihydro-2-benzofuranyl)methyl-3-(3-methoxyphenyl)-piperidine hydrochloride (28) was prepared analogously. m.p. 172°–4° C. (Found: C, 70.1; H, 7.05; N, 3.9; Cl, 9.95. $C_{21}H_{25}NO_2 \cdot HCl$ requires C, 70.1; H, 7.3; N, 3.9; Cl, 9.85').

The E.I. Mass spectrum showed M⁺ at m/e 323.

EXAMPLE 2

1-[2-(2-Benzofuryl)ethyl]-3-(3-methoxyphenyl)piperidine hydrochloride (3)

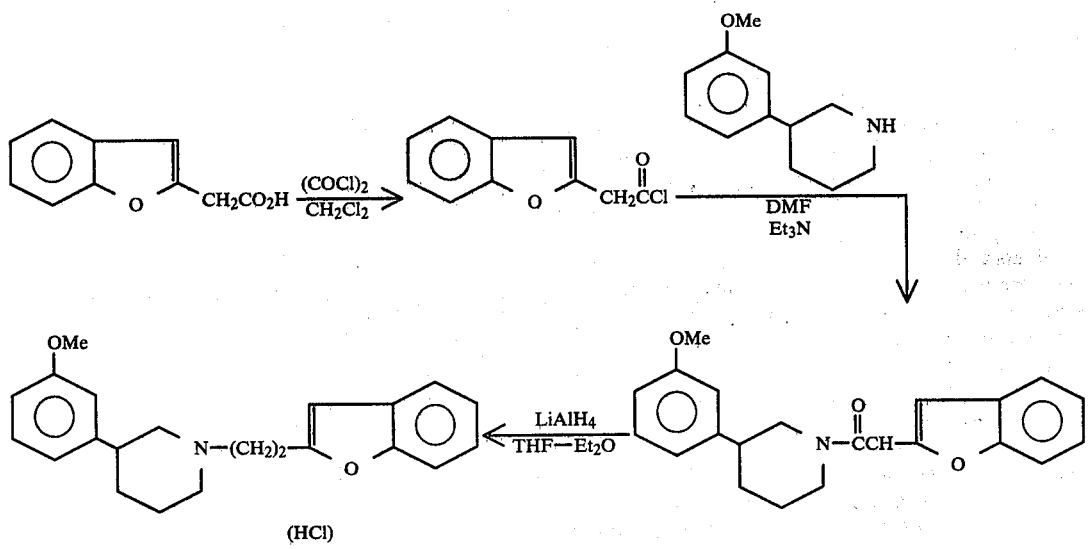

A solution of 2-benzofurylacetylchloride (prepared from 2-benzofurylacetic acid (2.0 g) and oxalyl chloride (3.3 g) in dichloromethane) in dichloromethane (20 ml) was added to a stirred solution of (3-methoxyphenyl)-3-piperidine (1.5 g) in dichloromethane (10 ml), DMF (10 ml) and triethylamine (5 ml) at 0° C. under nitrogen. The solution was stirred at this temperature for one hour and evaporated to dryness in vacuo. The residue was partitioned between dichloromethane and 10% sodium carbonate solution. The dichloromethane layer was washed with water, dried (Na₂SO₄) and chromatographed on alumina (Grade II, 200 g). Elution with ethyl acetatepentane (1:2) gave 1-(2-benzofurylacetyl)-3-(3-methoxyphenyl)-piperidine as an oil (2.1 g), ($\nu_{max}$ 1640 and 1660 cm⁻¹), a portion (1.7 g) of which was dissolved in dry tetrahydrofuran (20 ml) and dry ether (40 ml) and treated with lithium aluminium hydride (1.5 g) and the mixture was heated under gentle reflux for 1 hour. The mixture was cooled and cautiously treated with water (1.5 ml) followed by 10% sodium hydroxide (1.5 ml). The mixture was filtered and the precipitate washed well with dry ether. The filtrate was evaporated to dryness, treated with ethanolic-hydrogen chloride, and crystallised from ethyl acetate to affored 1-[2-

(2-benzofuryl)ethyl]-3-(3-methoxyphenyl)-piperidine hydrochloride (3), (1.55 g), m.p. 175°-176° C.

(Found: C, 70.7; H, 7.05; N, 3.7; Cl, 9.45% $C_{22}H_{35}NO_2$ HCl requires C, 71.05; H, 7.05, N, 3.75, Cl, 9.55%).

The following were prepared analogously:
1-(2-benzofurylmethyl)-3-(3-methoxphenyl) piperidine hydrochloride, m.p. 205°-206° (ethyl acetate) (4),
1-[2-(5-bromobenzofuryl)methyl]-3-(3-methoxyphenyl)-piperidine hydrochloride (29) mp 258°-259° C.
1-(3-methyl-2-benzofurylmethyl)-3-(3-methoxyphenyl)-piperidine hydrochloride (5),
1-(5-methoxy-2-benzofuryl methyl)-3-(3-methoxyphenyl)-piperidine hydrochloride (6),
1-[3-(2-benzofuryl)propyl]-3-(3-methoxy phenyl) piperidine hydrochloride (7).

EXAMPLE 3

1-[2-(1H-Indol-3-yl)ethyl]-3-(3-methoxyphenyl)piperidine hydrochloride hemihydrate (8)

A solution of (1H-indol-3-yl)acetyl chloride [prepared from (1H-indol-3-yl)acetic acid (1.25 g) and oxalyl chloride (1.75 g) in dichloromethane (200 ml) containing 1 drop of DMF] in dichloromethane (20 ml) was added dropwise to a stirred solution of (3-methoxyphenyl)-3-piperidine (1.5 g) in dichloromethane (40 ml), DMF (30 ml) and triethylamine (5 ml) at 0° C. under nitrogen. After 10 minutes the solution was evaporated to dryness in vacuo and the residue was partitioned between dichloromethane and sodium carbonate solution. The dichloromethane fraction was washed with water, dried ($Na_2SO_4$) and chromatographed on alumina (Grade II, 200 g). Elution of the column with ethyl acetate afforded 2-[(1H-indol-3-yl)acetyl]-3-(3-methoxyphenyl)-piperidine as an oil (1.1 g). A portion (0.9 g) was dissolved in dry tetrahydrofuran (20 ml) and dry ether (20 ml) and treated with lithium aluminium hydride (1.0 g) and the mixture was heated under gentle reflux for 1 hour. The cool solution was cautiously treated with water (1.0 ml) and 10% sodium hydroxide (1.0 ml) and the precipitate filtered and wased with dry ether. the filtrate was evaporated to dryness in vacuo, treated with ethanolichydrogen chloride and crystal-lised from ethanol-ethylacetate to afford 1-[2(1H-indol-3-yl)ethyl]-3-(3-methoxyphenyl)piperidine hydrochloride hemihydrate (0.8 g), m.p. 206°-208° C. (8) (Found C, 69.15; H, 7.4; N, 7.2. $C_{22}H_{26}N_2O\cdot HCl\ 0.5H_2O$ requires C, 69.55; H, 7.45; N, 7.4%).

1-(1H-indol-2yl)methyl-3-(3-methoxyphenyl)piperidine hydrochloride (9) and
1-[2-(1H-indol-2-yl)ethyl]-3-(3-methoxyphenyl)piperidine hydrochloride (10)
are prepared analogously.

EXAMPLE 4

3-[1-(2-bromo-3-benzofurylmethyl)-3-piperidyl]phenol hydrobromide (11)

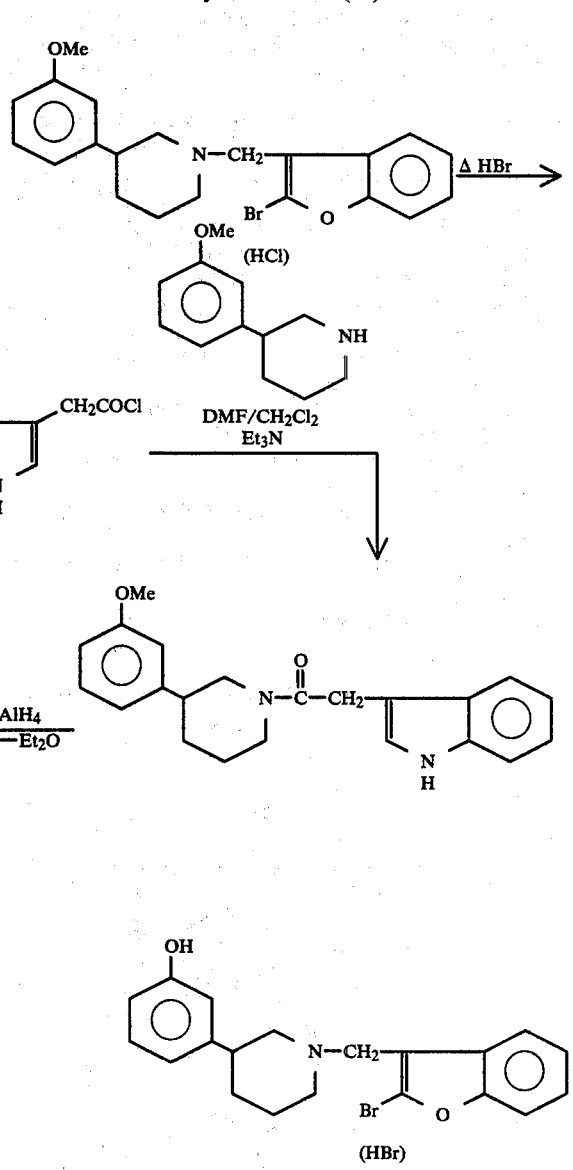

1-(2-Bromo-3-benzofurylmethyl)-3-(3-methoxyphenyl) piperidine hydrochloride (1) (0.65 g) in 48% hydrobromic acid (200 ml) was heated at 110°-115° C. for 1.5 hours under nitrogen, and evaporated to dryness in vacuo. The residue crystallised from ethanol-ether to afford 3-[1-(2-bromo-3-benzofurylmethyl)-3-piperidyl]-phenol hydrobromide (11) (0.6 g), m.p. 134°-140° C. (Found: M+ 385.0665. $C_{20}H_{20}NO_2Br$ requires M 385.0677).

The following were prepared analogously:

3-[1-(3-Benzofurylmethyl)-3-piperidyl]phenol hydrobromide hemihydrate (12), m.p. 128°-135° C. (from ethanol-ether) Found: M+ 307.1559. $C_{20}H_{21}NO_2$ requires M 307.1572) (Found: C, 60.8; H, 5.6; N, 3.5. $C_{20}H_{21}NO_2HBr0.5 H_2O$ requires C, 60.45, H, 5.85 N, 3.5%).

3-(1-[2-(2-Benzofuryl)ethyl]-3-piperidyl)phenol hydrobromide hemihydrate (13), m.p. 102°-108° C. (from ethanol-ether) (Found: C, 61.2; H, 5.9; N, 3.4 $C_{21}H_{23}NO_2.HBr$ 0.5 $H_2O$ requires: C, 61.3; H, 6.15; N, 3.4%), 3-[1-(2-benzofurylmethyl)-3-piperidyl]phenol hydrobromide (14), m.p. 110°-118° C. (from EtOH-Et$_2$O), 3-(1-[2-(1H-3-indolyl)ethyl]-3-piperidyl) phenol dihydrobromide (15), m.p. 210°-216° C. (Found: C, 52.85; H, 5.65; N, 5.75. $C_{21}H_{24}N_2O$ 2HBr requires C, 52.3; H, 5.45; N, 5.8%), 3-(1-[(2,3-Dihydro-2-benzofuranyl)methyl]-3-piperidinyl phenol) hydrobromide hydrate (30) m.p. 106°-110° C. (Found C, 59.3; H, 6.05; H, 31.5. $C_{20}H_{23}NO_2.HBr.H_2O$ requires C, 58.85; H, 6.4; N, 3.45%). The E I]) mass spectrum showed M+ at 309.1722. $C_{20}H_{23}NO_2$ requires M 309.1722.

3-(1-[2-(5-bromobenzofuryl)methyl]-3-piperidyl)phenol hydrobromide hemihydrate (31), mp 130°-138°.

3-(1-[2-(3-methylbenzofuryl)methyl]-3-piperidyl)phenol hydrobromide (16),

3-[1-(5-hydroxy-2-benzofurylmethyl)-3-piperidyl]phenol hydromide (17), (from (6))

3-(1-[3-(2-benzofuryl)propyl]-3-piperidyl)phenol hydrobromide (18),

3-[1-(1H-2-indolylmethyl)-3-piperidyl]phenol hydrobromide (19), 3-(1-[2-1H-2-indolyl)ethyl]-3-piperidyl)phenol hydrobromide (20)

are prepared analogously

EXAMPLE 5

3-{1-[3-(2-Brombenzofuryl)methyl]-3-piperidyl}phenyl benzoate hydrochloride (21)

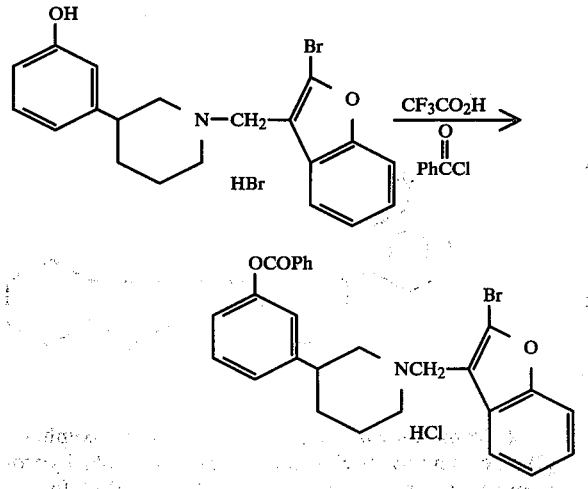

A solution of 3-{1-[3-(2-bromobenzofuryl)methyl]-3-piperidyl}phenol hydrobromide (11) (1.2 g) in trifluoroacetic acid (30 ml) is treated dropwise with benzoyl chloride (1.25 g) and the solution is heated under reflux under nitrogen for 2 hours, and evaporated to dryness in vacuo. The residue is treated with 10% sodium carbonate (100 ml) and extracted with ether (3×100 ml). The ether extract is washed with water, dried (Na$_2$SO$_4$), treated with ethereal hydrogen chloride and evaporated to dryness in vacuo. The resulting solid is trituated with ether and collected to afford (21).

The following are prepared analogously:

3-[1-(3-Benzofurylmethyl)-3-piperidyl]phenyl benzoate hydrochloride (22),

3-{1-[2-(2-benzofuryl)ethyl]-3-piperidyl}phenyl benzoate hydrochloride (23),

3-[1-(3-methyl-2-benzofurylmethyl)-3-piperidyl]phenyl benzoate hydrochloride (24), 3-[-(5-benzoyloxy-2-benzofurylmethyl)-3-piperidyl]-phenyl benzoate hydrochloride (25), 3-[1-(2-benzofurylmethyl)-3-piperidyl]phenyl benzoate hydrochloride (26), 3-(1-[3-(2-benzofuryl)propyl]-3-piperidyl)phenyl benzoate hydrochloride (27), 3-(1-(2,3-dihydro-2-benzofuranylmethyl)-3-piperidyl) phenyl benzoate hydrochloride (32)

3-(1-[2-(5-bromobenzofuryl)methyl]-3-piperidyl)phenyl benzoate hydrochloride (33).

EXAMPLE 6

Alternative route to free base of compound (15)

3-(1-[2-(1H-3-Indolyl)ethyl]-3-piperidyl)phenol (34)

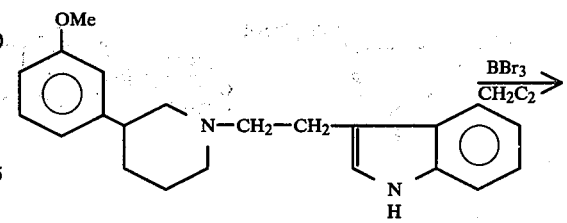

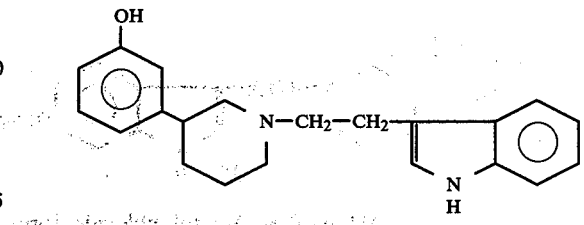

A solution of 1-[2-(1H-indol-3-yl)ethyl]-3-(3-methoxy phenyl) piperidine hydrochloride (1.4 g) in dichloromethane (500 ml) at −78° C. was treated dropwise with borontribromide (8 g) and the solution was allowed to warm up to room temperature over 2.5 hour. Water (5 ml) was added cautiously and the precipitate was filtered, washed with dichloromethane and water, dissolved in 10% sodium hydroxide solution (25 ml), acidified to pH 10 with 5N hydrochloric acid. The precipitate was collected, washed with water, to give 3-(1-[2-(1H-3-indolyl) ethyl]-3-piperidyl) phenol 1.2 g, m.p. 130°-135° C.

PHARMACOLOGY

Adrenoceptor and Dopamine Receptor Activity

α-Adrenoceptor and dopamine receptors were labelled using methods similar to those previously reported [see S. Lazareno and S. R. Nahorski, Communication presented to Brit. Pharm. Soc., Bradford, 74 (1981), and P. Greengrass and R. Bremer, Eur. J. Pharmacol 55, 323 (1979)]. Tested compounds showed displacement of 3-Prazosin, $3_H$-Yohimbine, 3H-Domperidone and $3_H$-Spiperone, indicating interaction with both α-adrenoceptor and dopamine receptors.

The inhibition constants (Ki) for compound (30) compared to the well known dopamine agonist A-6, 7-DTN and A-5, 6-DTN are shown below.

| | INHIBITION CONSTANT Ki (M) | | | |
|---|---|---|---|---|
| Compound | $3_H$-Yohimbine | $3_H$-Prazosin | $3_H$-Domperidone | $3_H$-Spiperone |
| (30) | $1.3 \times 10^{-8}$ | $2.1 \times 10^{-7}$ | $4.8 \times 10^{-8}$ | $2.0 \times 10^{-7}$ |
| A-6,7-DTN | $5.6 \times 10^{-7}$ | $1.0 \times 10^{-5}$ | $1.2 \times 10^{-8}$ | $1.3 \times 10^{-7}$ |
| A-5,6-DTN | $6.9 \times 10^{-7}$ | $1.6 \times 10^{-5}$ | $2.4 \times 10^{-7}$ | $5.2 \times 10^{-7}$ |

Inhibition of Spontaneous Climbing in the Mouse

Tested compounds inhibited the spontaneous climbing behaviour of mice. It is believed that this inhibitory effect is mediated by stimultion of presynaptic dopaminergic autoreceptors, i.e. receptors whose stimulation results in inhibition of dopamine synthesis and electrical activity of dopamine neurones. Spontaneous climbing behavior was assessed by the method of M. P. Martres et al., *Brain Res*, 136, 319 (1977).

This involves the monitoring of the frequency of climbing behaviour of mice in inverted food hoppers over a 10 minute period commencing 3 minutes after subcutaneous administration of compound.

A climb is defined as the mouse having all four feet off the ground. Experiments are carried out with a minimum of 5 groups of 10 mice, one group acting as control. The number of climbs exhibited by the drug-treated group is expressed as a percentage change from the number exhibited by the control group. The $ID_{50}$ value is calculated using the Litchfield and Wilcoxon technique and is defined as the concentration of drug which would be expected to reduce spontaneous climbing of a group of mice by 50%.

| Compound | % Inhibition of Spontaneous Climbing Behaviour in Mice |
|---|---|
| (30) | $ID_{50}$ - 0.09 mg/kg |
| (11) | 24% at 0.2 mg/kg |
| (12) | 23% at 0.2 mg/kg |
| (13) | $ID_{50}$ - 0.29 mg/kg |
| (14) | $ID_{50}$ - 1.7 mg/kg |
| (34) | 52% at 0.2 mg/kg |

Toxicity

No toxic effects were observed in the above tests.

I claim:

1. A compound of the formula (I), or a pharmaceutically acceptable salt thereof:

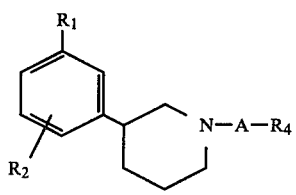

wherein
$R_1$ is hydroxy, $C_{1-4}$ alkoxy or a pharmaceutically acceptable in-vivo hydrolysable acyloxy group;

$R_2$ is hydrogen, $C_{1-4}$ alkyl, hydroxy, $C_{1-4}$ alkoxy or an in-vivo hydrolysable acyloxy group;

$R_4$ is benzofuryl, benzothienyl, indolyl, quinolyl, isoquinolyl, 2,3-dihydrobenzofuryl, 2,3-dihydrobenzylthienyl or 2,3-dihydroindolyl optionally substituted by one or two substituents selected from $C_{1-4}$ alkoxy, hydroxy, acyloxy, trifluoromethyl, halogen or nitro; and A is a bond or $C_{1-6}$ alkylene.

2. A compound according to claim 1 of formula (IX):

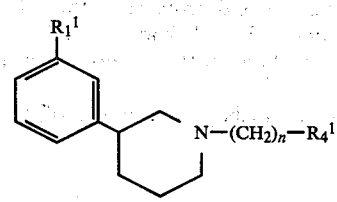

wherein:
$R_1{}^1$ is hydroxyl or a pharmaceutically acceptable in-vivo hydrolysable acyloxy group;
$R_4{}^1$ is benzofuryl, benzothienyl, indolyl, quinolyl or isoquinolyl, optionally substituted by one or two substituents selected from $C_{1-4}$ alkoxy, hydroxy, acyloxy, trifluoromethyl, halogen or nitro; and n is 0 to 4.

3. A compound according to claim 1 of formula (X):

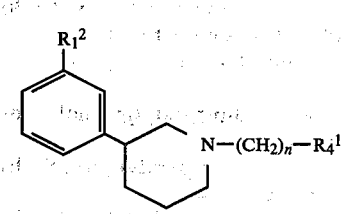

wherein:
$R^2{}_1$ is $C_{1-4}$ alkoxy;
$R_4{}^1$ is benzofuryl, benzothienyl, indolyl, quinolyl or isoquinolyl, optionally substituted by one or two substituents selected from $C_{1-4}$ alkoxy, hydroxy, acyloxy, trifluoromethyl, halogen or nitro; and n is 0 to 4.

4. A compound according to claim 2 of formula (XI)

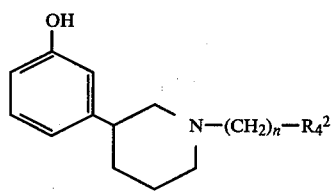

$R^2{}_4$ is benzofuryl or indolyl, optionally substituted on the heterocycle by $C_{1-4}$ alkyl or halogen, and n is 0 to 4.

5. A compound according to claim 1 of formula (XIX):

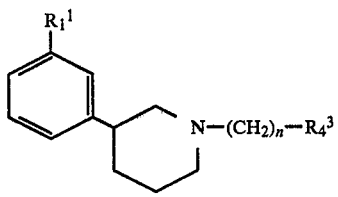

wherein:

$R_1^1$ is hydroxyl or a pharmaceutically acceptable in-vivo- hydrolysable acyloxy group:

$R_4^3$ is 2,3-dihydrobenzofuryl, 2,3-dihydrobenzothienyl or 2,3-dihydroindolyl optionally substituted by one or two substituents selected from $C_{1-4}$ alkoxy, hydroxy, acyloxy, trifluoromethyl, halogen or nitro; and n is 0 to 4.

6. A compound according to claim 1 of formula (XXI):

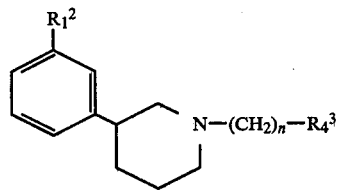

wherein: $R^3{}_4$ is 2,3-dihydrobenzofuryl, 2,3-dihydrobenzothienyl or 2,3-dihydroindolyl optionally substituted by one or two substituents selected from $C_{1-4}$ alkoxy, hydroxy, acyloxy, trifluormethyl, halogen or nitro, and n is 0–4; and $R_1^2$ is $C_{1-4}$ alkoxy.

7. 3-{1-[(2,3-Dihydro-2-benzofuranyl)methyl]-3-piperidinyl}phenol hydrobromide hydrate, 3-[1-(2-bromo-3-benzofurylmethyl)-3-piperidyl] phenol hydrobromide, 3-[1-(3-benzofurylmethyl)-3-piperidyl]phenol hydrobromide hemihydrate, 3-(1-[2-(2-benzofuryl)ethyl]-3-piperidyl)phenol hydrobromide hemihydrate, 3-[1-(2-benzofurylmethyl)-3-piperidyl]phenol hydrobromide, or 3-(1-[2-(1H-3-indolyl)ethyl]-3-piperidyl) phenol dihydrobromide, or a corresponding free base.

8. A pharamaceutical composition useful for the treatment of central nervous system disorders in mammals including humans which comprises a therapeutically effective amount of a compound of the formula (I), or a pharmaceutically acceptable salt thereof:

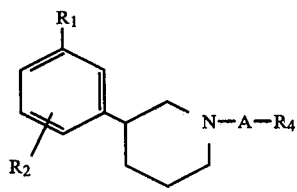

wherein:

$R_1$ is hydroxy, $C_{1-4}$ alkoxy or a pharmaceutically acceptable in-vivo hydrolysable acyloxy group: wherein:

$R_1$ is hydroxy, $C_{1-4}$ alkoxy or a pharmaceutically acceptable in-vivo hydrolysable acyloxy group:

$R_2$ is hydrogen, $C_{1-4}$ alkyl, hydroxy, $C_{1-4}$ alkoxy or a pharmaceutically acceptable in-vivo hydrolysable acyloxy group;

$R_4$ is benzofuryl, benzothienyl, indolyl, quinolyl, isoquinolyl,2,3-dihydrobenzofuryl, 2,3-dihydrobenzylthienyl or 2,3-dihydroindolyl optionally substituted by one or two substituents selected from $C_{1-4}$ alkoxy, hydroxy, acyloxy, trifluoromethyl, halogen or nitro; and A is a bond or $C_{1-6}$ alkylene, in combination of with a pharmaceutically acceptable carrier.

9. A composition according to claim 8 wherein the compound is of the formula (IX):

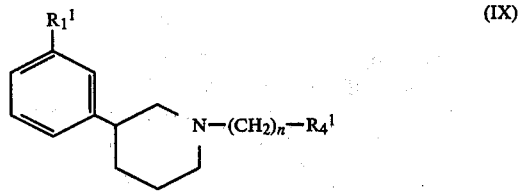

wherein:

$R_1^1$ is hydroxyl or a pharmaceutically acceptable in-vivo hydrolysable acyloxy group;

$R_4^1$ is benzofuryl, benzothienyl, indolyl, quinolyl or isoquinolyl, optionally substituted by one or two substituents selected from $C_{1-4}$ alkoxy, hydroxy, acyloxy, trifluoromethyl, halogen or nitro; and n is 0–4.

10. A composition according to claim 8 wherein the compound is of the formula (X):

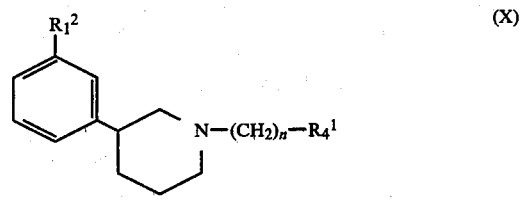

wherein:

$R^2{}_1$ is $C_{1-4}$ alkoxy;

$R_4^1$ is benzofuryl, benzothienyl, indolyl, quinolyl or isoquinolyl, optionally substituted by one or two substituents selected from $C_{1-4}$ alkoxy, hydroxy, acyloxy trifluoromethyl, halogen or nitro, and n is 0 to 4.

11. A composition according to claim 9 wherein the compound is of the formula (XI).

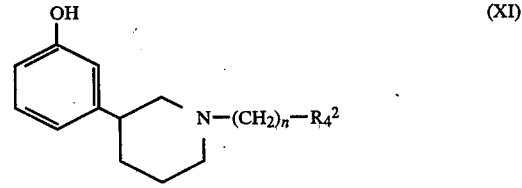

$R^2{}_4$ is benzofuryl or indolyl, optionally substituted on the heterocycle by $C_{1-4}$ alkyl or halogen, and n is 0 to 4.

12. A composition according to claim 8 wherein the compound is of the formula (XIX):

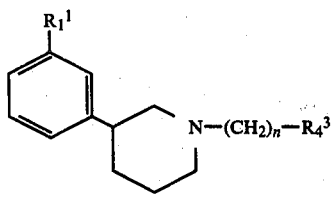

wherein:

R¹1 is hydroxyl or a pharmaceutically in-vivo hydrolysable acyloxy group;

R₄³ is 2,3-dihydrobenzofuryl, 2,3-dihydrobenzothienyl or 2,3-dihydroindolyl optionally substituted by one or two substituents selected from $C_{1-4}$ alkoxy, hydroxy, acyloxy, trifluoromethyl, halogen or nitro; and n is 0–4.

13. A composition according to claim 8 wherein the compound is of the formula (XXI):

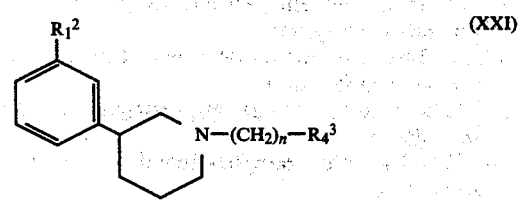

wherein: R₄³ is 2,3-dihydrobenzofuryl, 2,3-dihydrobenzothienyl or 2,3-dihydroindolyl optionally substituted by one or two substituents selected from $C_{1-4}$ alkoxy, hydroxy, acyloxy, trifluormethyl, halogen or nitro, and n is 0–4; and R₁² is $C_{1-4}$ alkoxy.

14. A composition according to claim 8 wherein the compound is:
3-{1-[(2,3-Dihydro-2-benzofuranyl)methyl]-3-piperidinyl}phenol hydrobromide hydrate,
3-[1-(2-bromo-3-benzofurylmethyl)-3-piperidyl] phenol hydrobromide,
3-[1-(3-benzofurylmethyl)-3-piperidyl]phenol hydrobromide hemihydrate,
3-(1-[2-(2-benzofuryl)ethyl]-3-piperidyl)phenol hydrobromide hemihydrate,
3-[1-(2-benzofurylmethyl)-3-piperidyl]phenol hydrobromide, or
3-(1-[2-(1H-3-indolyl)ethyl]-3-piperidyl) phenol dihydrobromide, or a corresponding free base.

15. A method of treating dopamine-dependent CNS disorders in mammals including humans which comprises administering to such a mammal in need thereof a therapeutically effective amount of a compound of the formula I, or a pharmaceutically acceptable salt thereof:

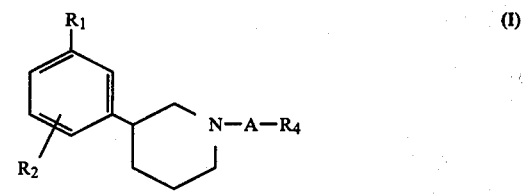

wherein R₁ is hydroxy, $C_{1-4}$ alkoxy or a pharmaceutically acceptable in-vivo hydrolysable acyloxy group: wherein R₁ is hydroxy, $C_{1-4}$ alkoxy or a pharmaceutically acceptable in-vivo hydrolysable acyloxy group;

R₂ is hydrogen, $C_{1-4}$ alkyl, hydroxy, $C_{1-4}$ alkoxy or a pharmaceutically acceptable in-vivo hydrolysable acyloxy group;

R₄ is benzofuryl, benzothienyl, indolyl, quinolyl, isoquinolyl,2,3-dihydrobenzofuryl, 2,3-dihydrobenzylthienyl or 2,3-dihydroindolyl optionally substituted by one or two substituents selected from $C_{1-4}$ alkoxy, hydroxy, acyloxy, trifluoromethyl, halogen or nitro; and A is a bond or $C_{1-6}$ alkylene, in combination of a pharmaceutically acceptable carrier.

16. A method according to claim 15 wherein the compound is of the formula (IX):

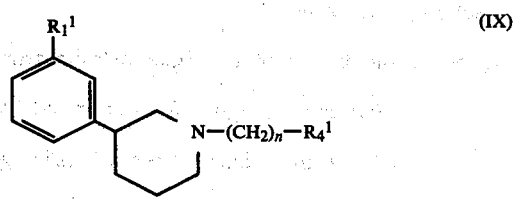

wherein:

R₁¹ is hydroxyl or a pharmaceutically acceptable in-vivo hydrolysable acyloxy group;

R₄¹ is benzofuryl, benzothienyl, indolyl, quinolyl or isoquinolyl, optionally substituted by one or two substituents selected from $C_{1-4}$ alkoxy, hydroxy, acyloxy, trifluoromethyl, halogen or nitro; and n is 0–4.

17. A method according to claim 15 wherein the compound is of the formula (X):

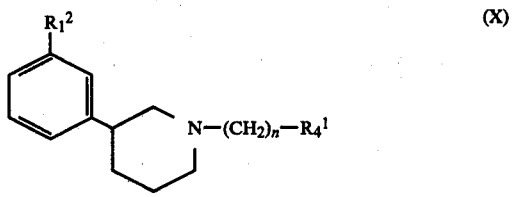

wherein:

R²₁ is $C_{1-4}$ alkoxy;

R₄¹ is benzofuryl, benzothienyl, indolyl, quinolyl or isoquinolyl, optionally substituted by one or two substituents selected from $C_{1-4}$ alkoxy, hydroxy, acyloxy trifluoromethyl, halogen or nitro, and n is 0 to 4.

18. A method according to claim 16 wherein the compound is of the formula (XI).

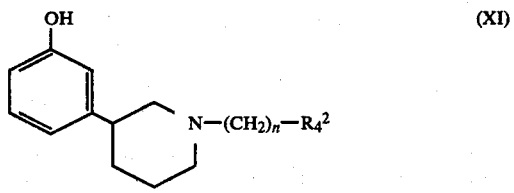

R²₄ is benzofuryl or indolyl, optionally substituted on the heterocycle by $C_{1-4}$ alkyl or halogen, and n is 0 to 4.

19. A method according to claim 8 wherein the compound is of the formula (XIX):

(XIX)

wherein:

R$_1^1$ is hydroxy or a pharmaceutically in-vivo hydrolysable acyloxy group;

R$_4^3$ is 2,3-dihydrobenzofuryl, 2,3-dihydrobenzothienyl or 2,3-dihydroindolyl optionally substituted by one or two substituents selected from C$_{1-4}$ alkoxy, hydroxy, acyloxy, trifluoromethyl, halogen or nitro; and n is 0–4.

20. A method according to claim 15 wherein the compound is of the formula (XXI):

(XXI)

wherein: R$_4^3$ is 2,3-dihydrobenzofuryl, 2,3-dihydrobenzothienyl or 2,3-dihydroindolyl optionally substituted by one or two substituents selected from C$_{1-4}$ alkoxy, hydroxy, acyloxy, trifluoromethyl, halogen or nitro, and n is 0–4; and R$_1^2$ is C$_{1-4}$ alkoxy.

21. A method according to claim 8 wherein the compound is:
3-{1-[(2,3-Dihydro-2-benzofuranyl)methyl]-3-piperidinyl}phenol hydrobromide hydrate,
3-[1-(2-bromo-3-benzofurylmethyl)-3-piperidyl]phenol hydrobromide,
3-[1-(3-benzofurylmethyl)-3-piperidyl]phenol hydrobromide hemihydrate,
3-(1-[2-(2-benzofuryl)ethyl]-3-piperidyl)phenol hydrobromide hemihydrate,
3-[1-(2-benzofurylmethyl)-3-piperidyl]phenol hydrobromide, or
3-(1-[2-(1H-3-indolyl)ethyl]-3-piperidyl) phenol dihydrobromide,
or a corresponding free base.

* * * * *